United States Patent [19]

Weyns et al.

[11] 4,306,458
[45] Dec. 22, 1981

[54] APPARATUS FOR OBJECT SCANNING

[75] Inventors: Arthur Weyns, Muizen, Belgium; Alfred Walz, Burgthann, Fed. Rep. of Germany

[73] Assignee: Siemens Aktiengesellschaft, Berlin & Munich, Fed. Rep. of Germany

[21] Appl. No.: 43,142

[22] Filed: May 29, 1979

[30] Foreign Application Priority Data

Jun. 15, 1978 [DE] Fed. Rep. of Germany ....... 2826263

[51] Int. Cl.³ ............................................. G01N 29/00
[52] U.S. Cl. .................................. 73/621; 33/1 CC; 128/660
[58] Field of Search ................ 73/621, 634; 33/1 CC, 33/1 MP, 1 PT; 128/660

[56] References Cited

U.S. PATENT DOCUMENTS

| 2,906,179 | 9/1959 | Bower .................................. 33/1 CC |
| 3,308,652 | 3/1967 | Appel et al. . |
| 3,439,530 | 4/1969 | Flaherty .......................... 73/621 X |
| 3,448,606 | 6/1969 | Flaherty et al. . |
| 3,944,798 | 3/1976 | Eaton . |
| 4,014,207 | 3/1977 | Meyer et al. .......................... 73/621 |

FOREIGN PATENT DOCUMENTS 2620793 11/1976 Fed. Rep. of Germany .
2724998 12/1977 Fed. Rep. of Germany .

OTHER PUBLICATIONS

W. Bopp et al., "Radar, Grundlagen und Anwendungen", 1962, Fachverlag Schiele & Schön GmbH, Berlin, pp. 159-172.

Primary Examiner—James J. Gill
Attorney, Agent, or Firm—Hill, Van Santen, Steadman, Chiara & Simpson

[57] ABSTRACT

In an exemplary embodiment, an ultrasonic scanning apparatus has an articulated support for at least one scan head and angle indicators for determining point- and/or direction-coordinates of the scanning. An angle detection and processing is desired which is considerably simplified as compared with the state of the art but which is nevertheless highly precise, interference-insensitive and cost-economical. This is achieved by at least one synchro system for supplying a sine and/or cosine of the angular value of the rotational angles and including a purely electric cascade interconnection of individual synchros so as to form a synchro control transformer- or resolver-chain or a mixed chain consisting of synchro control transformer- or resolver-chain or a mixed chain consisting of synchro control transformers and resolvers for the purpose of conversion of sine- or cosine-values, respectively, of the rotational angles into sums and/or differences of individual angles and/or into sine- or cosine-functions, respectively, of such angular sums or angular differences.

3 Claims, 12 Drawing Figures

APPARATUS FOR OBJECT SCANNING

BACKGROUND OF THE INVENTION

The invention relates to an apparatus for object scanning, in particular, an ultrasonic-scanning apparatus, comprising an articulated support for at least one scan head, particularly an ultrasonic head, and comprising an installation with angle indicators associated with the joints of the articulated support for the purpose of detecting point and/or directional coordinates of the scanning, given a random space positioning of the scan head, in dependence upon angular signals of the angle indicators.

To be included in the category of apparatus of this type are all those which permit, in any form, scannings of examination objects with the aim e.g. of determining the object outline, detecting object sectional planes, ascertaining direction or distance, respectively, of objects or the like in which a bearing is to be taken. All these forms of scanning basically amount to the detection of point and/or directional coordinates of the respective scanning. The scanning can proceed directly by means of a mechanical scan head on the object. However, it can also proceed by means of scanning media, such as light (e.g. laser), thermal radiation, sound, or the like. Of particular interest is scanning by means of ultrasound, whereby the apparatus for object scanning is then an ultrasonic scanning apparatus, and the scan head is an ultrasonic head.

Particularly with regard to ultrasonic scanning, ultrasonic sectional image apparatus are known which, for the detection of point coordinates and/or directional coordinates of the ultrasonic scanning, employ either the angular measurement relative to a horizontal or a vertical line, or the angular measurement between the successive elements of the articulated support (included angle, or complement of this angle, respectively).

The angular measurement relative to a horizontal or a vertical line (e.g. according to U.S. Pat. No. 3,924,452) indeed permits, on account of the simple coordinate relations, the utilization of angle indicators directly for the angle or such for the sine or cosine, respectively, of the angle (sine-cosine-potentiometers as angle indicators); however, the change in the angles must be mechanically transmitted at a fixed reference point; for example, by means of a cable or by means of a pantograph system similar to that of a drafting machine. The mechanical system must be highly precise and interference-insensitive with regard to temperature influences or also slippage. These conditions, of course, increase the cost of the entire system.

Up to the present time, the measurement of angles between the successive pivotally connected support elements is successful, in an analog fashion, only with a series-connection of potentiometers; or, in a digital fashion, with incremental angle indicators. However, a series-connection of potentiometers requires much space; moreover, it is expensive and very temperature-sensitive. Digital angle gauges are likewise high in cost-outlay, as well as temperature- and interference-sensitive. In addition, they require as a precondition the application of a computer (e.g. according to the article "A Computer-Controlled Ultrasound Image-Forming System" of S. Schorum, H. Fidel, from Searle Ultrasound, Santa Clara, Calif.).

SUMMARY OF THE INVENTION

It is the object of the present invention, in the case of an apparatus for object scanning of the type initially cited, to provide an installation for detecting point coordinates and/or direction coordinates of the scanning which manages with an angular measurement which is greatly simplified as compared with the state of the art and which is nevertheless highly precise, interference-insensitive, and more favorable in price.

In accordance with the invention, the object is achieved by at least one synchro system with a synchro preferably at every joint of the articulated support, said synchros supplying a sine and/or cosine function of the angular value of the rotational angle at the joint, and with a purely electric cascade interconnection of individual or several synchros to form a synchro control transformer- or resolver-chain, or a mixed chain consisting of synchro control transformers and resolvers for the purpose of converting sine or cosine values of detected rotational angles into sums and/or differences of individual angles and/or into sine or cosine functions of such angular sums, or angular differences, respectively.

The invention operates with synchros as angular indicators which, by means of a simple series-connection—i.e., in a purely electrical manner—supply the desired angle combination values as a synchro control transformer chain or resolver chain.

Synchros are, moreover, very stable, not susceptible to trouble (or failure); they manifest minimum spatial dimensions, and are more favorable in price in comparison with digital angle indicators. In contrast with incremental digital systems, the correct angular information is immediately present with the switching-on of the system. The introduction of synchros in the inventive sense thus not only simplifies the angle indication to a considerable extent; the entire angular measurement is very precise, it is less sensitive to interference and the introduction of the new angle gauges is altogether more economical in cost.

Connections of synchros in series as a synchro control transformer—or also resolver-chain—are no longer new per se. Such chains are prior knowledge e.g. from "Technical Information For The Engineer" of the Singer Company, Little Falls, United States, 1967, or from the Siemens publication "Siemens-Drehmelder" from the year 1970. However, it must be borne in mind that all of the described application possibilities for synchro control transformer chains, or resolver chains, respectively, are restricted to so-called angle follow-up controls. Such follow-up controls principally operate such that a specified rotating object, which is disposed at s specific distance, is to be readjusted to a specified angle (application e.g. radar technology, radio link system technology, or the like). In such a case, the motors of the synchro control transformer chain or also the resolver chain serve the purpose of transmitting this angle (or also angular sums or differences) which, for this purpose, is fed into the respectively first motor of the chain, and from there, is conveyed—true-to-nature—to the respectively last motor of the chain as a rotary drive for the object to be rotated. The synchro control transformer chains, or resolver chains, respectively, of the state of the art thus basically differ from the present invention in the problem-statement and in the solution.

Further advantages and details of the invention are apparent from the following description of exemplary embodiments on the basis of the accompanying drawings in conjunction with the subclaims; and other objects, features and advantages will be apparent from this detailed disclosure and from the appended claims.

DETAILED DESCRIPTION

Figure 1:
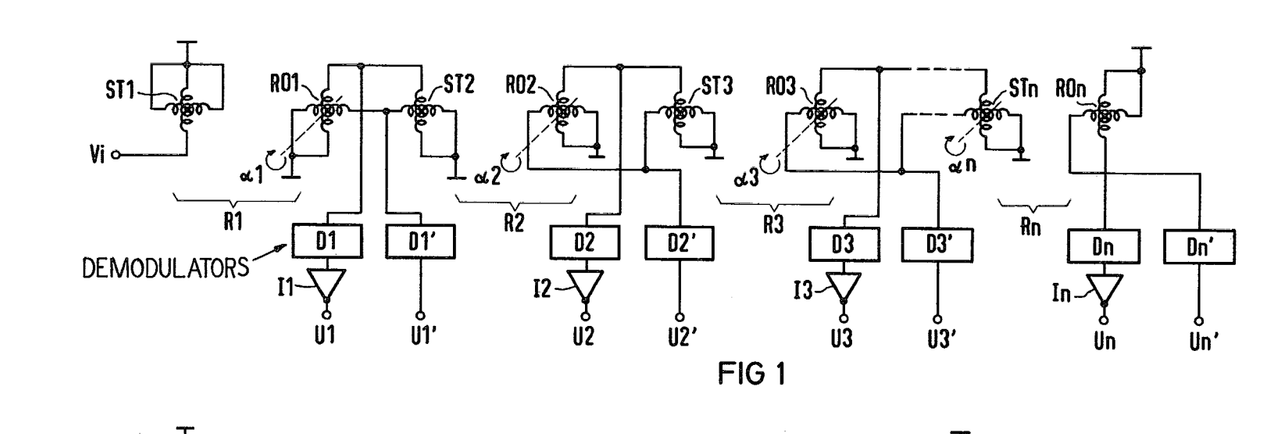
FIGS. 1 and 2 illustrate basic circuits of a resolver chain for determining the sine or cosine of angular sums, on the one hand, and angular differences, on the other hand.
Figure 2:
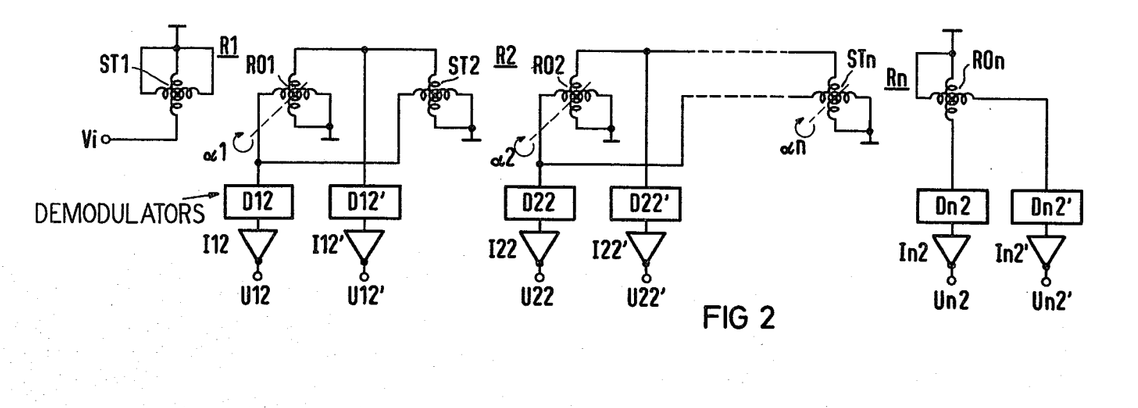

In the resolver chains of FIGS. 1 and 2, the stator windings with the respective rotor windings of every synchronous motor in the series-connection are designated from left to right with an increasing number, with ST1, RO1, ST2, RO2; ST3, RO3 ... STn, ROn, respectively. The individual resolvers bear the designations R1, R2, R3 ... Rn. The input supply a.c. voltage of the chain is indicated with Vi. The rotational angles of the individual rotors are designated by $\alpha 1, \alpha 2, \alpha 3 \ldots \alpha n$.

In the specific interconnection of FIG. 1, after demodulation in demodulators D1, D1'; D2, D2'; D3, D3' ... Dn, Dn', and inverting in inverter members I1, I2, I3 ... In, the cosine—or sine-functions, respectively, of angles and angular sums result as follows:

$U1 = K1 \cos \alpha 1$ $U1' = K1 \sin \alpha 1$ $U2 = K1K2 \cos (\alpha 1 + \alpha 2)$ $U2' = K1K2 \sin (\alpha 1 + \alpha 2)$ $U3 = k1k2k3 \cos (\alpha 1 + \alpha 2 + \alpha 3)$ $U3' = k1k2k3 \sin (\alpha 1 + \alpha 2 + \alpha 3)$ $Un = k1k2 \ldots kn \cos (\alpha 1 + \alpha 2 + \ldots + \alpha n)$ $Un' = k1k2 \ldots kn \sin (\alpha 1 + \alpha 2 + \ldots + \alpha n)$ Correspondingly, in the embodiment of FIG. 2, after demodulation in demodulators D12, D12'; D22, D22' ... Dn2, Dn2' and inverting in inverter members I12, I12'; I22, I22' ... In2, In2' the sine- or cosine-functions, respectively, of angles or angular differences result as follows:

$U12 = k1 \sin \alpha 1$ $U12' = k1 \cos \alpha 1$ $U22 = k1k2 \sin (\alpha 1 - \alpha 2)$ $U22' = k1k2 \cos (\alpha 1 - \alpha 2)$ $Un2 = k1k2 \ldots kn \sin (\alpha 1 - \alpha 2 - \ldots - \alpha n)$ $Un2' - k1k2 \ldots kn \cos (\alpha 1 - \alpha 2 - \ldots - \alpha n)$ The constants k1, k2, k3 ... kn are, in both instances, the transmission factors of the individual resolvers R1, R2 ... Rn.

Figure 3:
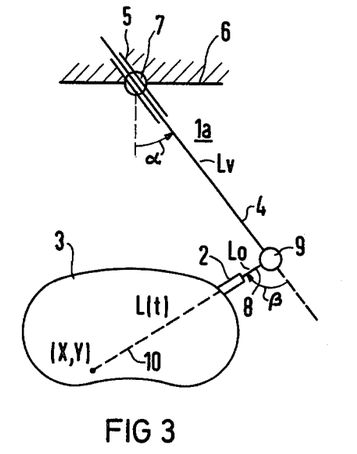
FIG. 3 illustrates the basic diagram of an object scanning (in the present case, ultrasonic-compound scan) comprising a two-armed articulated support for a scan head.

FIG. 3 illustrates a basic diagram of an object scanning system (in the present instance, ultrasonic compound-scan) with a two-arm articulated support 1a for a scan head 2 (ultrasonic-scan head). Specifically in the case of compound-scan, during a scanning operation, the positions of the sonic head 2 on the surface of the examination object 3 (human body), as well as the irradiation direction into the object, must be continuously detected (or determined), since the echoes of the sonic pulses along every sonic beam path are to be reproduced true-to-location in the form of brightness- (or intensity-) modulated lines on the viewing screen of an oscilloscope tube.

Specifically in the exemplary embodiment of FIG. 3, the coordinate determination in the scanning plane proceeds by means of one linear measurement and two angular measurements. The double-joint arm 1a, accordingly, consists of a first arm section 4 which is arranged such that it is capable of longitudinal displacement in a longitudinal guide 5 on an arm support-mounting 6 (floor stand or ceiling support), and which is rotatable through the angle α by means of a first rotating joint (or pivot mounting) 7. The length of the first arm section between the pivot axes at 7 and 9 is designated by Lv. As support element for the ultrasonic head 2 there is a second arm section 8 which is rotatably linked to the first arm section 1 by means of a second rotating joint (or pivot mounting) 9. The length of the second arm section is designated by Lo, the rotational angle is correspondingly referenced by β. In the examination object 3, a transmitted ultrasonic pulse, or the echo pulses returning due to this sonic pulse, respectively, extend along the beam direction 10. A random point on the line representing this beam direction 10 has the coordinates X, Y. The depth of the respective point X, Y, in the object 3 is referenced by L (t). Since, during the echo-image-formation on the viewing screen of the oscilloscope tube, all echo coordinates along the beam direction 10 are to be reproduced in the form of an image, L (t) is, accordingly, a linear function of time (sawtooth function).

With the illustrated double-joint arm as the support for the ultrasonic scan head 2, there result, in dependence upon the lengths Lv and Lo of the arm parts, as well as the respectively adjusted angles $\alpha$ and $\beta$, the scanning coordinates for a random scanning point in the object 3 as follows:

$$X = Lv \sin \alpha + [Lo + L(t)] \sin (\alpha + \beta)$$

$$Y = Lv \cos \alpha + [Lo + L(t)] \cos (\alpha + \beta)$$

Figure 4:
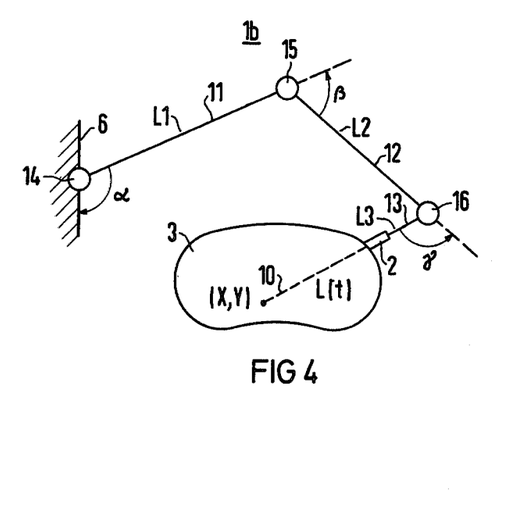
FIG. 4 illustrates the basic diagram of a corresponding scanning by means of a three-armed articulated support.

Correspondingly, for the three-arm articulated support 1b of FIG. 4 the continuous coordinate relations result at:

$$X = L1 \sin \alpha + L2 \sin (\alpha + \beta) + [L3 + L(t)] \sin (\alpha + \beta + \gamma)$$

$$Y = L1 \cos \alpha + L2 \cos (\alpha + \beta) + [L3 + L(t)] \cos (\alpha + \beta + \gamma),$$

wherein L1, L2, L3 are the lengths of the individual arms 11, 12 and 13 of the support; L(t) the depth position of the coordinate point X, Y, in the examination object 3, and the angles $\alpha$, $\beta$ and $\gamma$ are the rotational angles for the rotation of the individual arms about rotating joints 14, 15 and 16.

Figure 5:
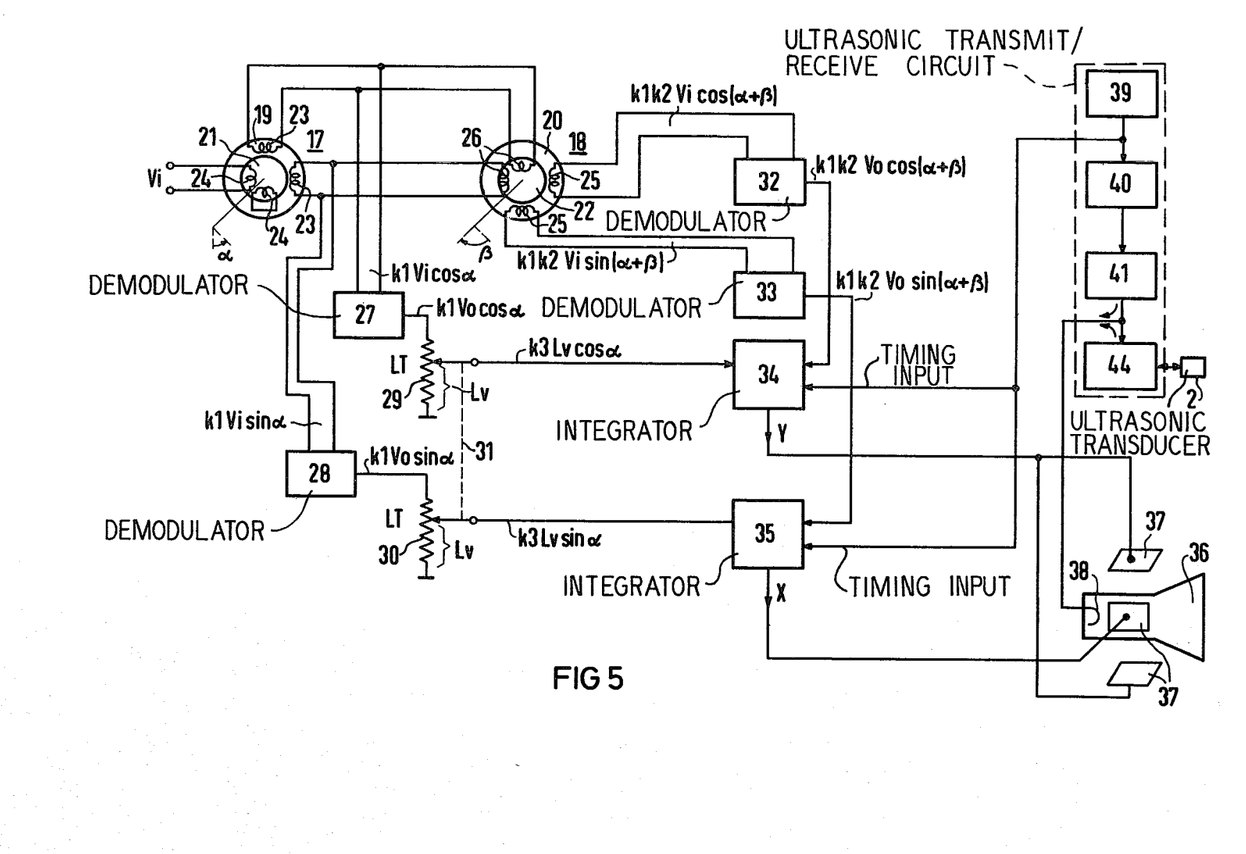
FIG. 5 illustrates an exemplary embodiment, tailored to scanning by means of a two arm support according to FIG. 3, comprising a resolver chain for an ultrasonic scanning apparatus in a basic circuit diagram.

FIG. 5 illustrates an exemplary embodiment adapted to the double-joint arm of FIG. 3, comprising a resolver chain for an ultrasonic scanning apparatus. According to the two hinge joints 7 and 9 of the double joint arms of FIG. 3, the arm comprises a total of two synchros 17 and 18, consisting of the stators 19 and 20, respectively, and the rotors 21 and 22, respectively. The synchro 17 correspondingly comprises, for its stator, the stator windings 23, and for its rotor 21, the rotor windings 24. Correspondingly, the synchro 18 comprises, for the stator 20, the stator windings 25, and for the rotor 22, the rotor windings 26. The two synchros 17 and 18 are introduced as angle indicators into the rotary joints 7 and 9 of the double joint arm of FIG. 3. The synchros function as resolvers, and thus form a resolver chain in the illustrated interconnection.

Corresponding to the illustration of FIG. 5, the cosine function and sine function of the angle $\alpha$ at joint 7 are determined by means of the resolver 17. The two outputs of this resolver deliver the output voltages k1 Vi cos $\alpha$ and k1 Vi sin $\alpha$, wherein, as already explained above, k1 is again the transmission factor of the resolver 17, and Vi is the input signal. Since synchros are exclusively operated with a.c. voltage, the input signal Vi is an a.c. signal according to the relation Vi = Vo·sin $\omega$t. In the case of the output of the resolver 17, the angular information is contained in the amplitude of the a.c. signal. By means of demodulators 27 and 28, one obtains (corresponding to basic circuit diagram of FIG. 1), finally, d.c. voltage signals k1 Vo sin $\alpha$ and k1 Vo cos $\alpha$. These signals are fed into one potentiometer 29 or 30, each, which generates an output signal corresponding to the length Lv of the first longitudinally displaceable arm 4. The mechanical coupling of both potentiometers 29 and 30 with the longitudinal displacement of the arm 4 is indicated by 31. With the adjustment of the potentiometers to the length Lv, the desired factors Lv cos $\alpha$ and Lv sin $\alpha$ are obtained multiplied with a constant k3. k3 is here the ratio of k1 Vo to the overall length LT of the arm 4 (total resistance of the potentiometers 29 or 30, respectively).

If, moreover, the output signals of the resolver 17 are additionally supplied as input signals to the resolver 18 which is disposed in the rotary joint 9, then two output signals are obtained from the series-connection of the two resolvers 17 and 18, whose amplitude contains the cosine and sine function of the angular arm. The constant k2 is the transmission factor of the resolver 18. After demodulation in the demodulators 32 and 33, the magnitudes proportional to k1 k2 sin $(\alpha + \beta)$ and k1 k2 cos $(\alpha + \beta)$ are available. If, as illustrated, these signals are now fed, as input signals, into one integrator 34 and 35 each, and the two other signals k3 Lv sin $\alpha$ and k3 Lv cos $\alpha$ are fed into the integrators as initial conditions, the output signals of the integrators 34 and 35, given a corresponding selection of the amplification and the constants of the signals for initial condition and integration, represent the two coordinate formulas for X and Y. If these X- and Y-signals are applied to the deflecting plates (or deflecting coils) of a cathode ray tube, one obtains, given a corresponding brightness (or intensity) modulation, in dependence upon occurring echo signals, the desired coordinate-true ultrasonic image. In FIG. 5, the cathode ray tube is referenced by 36; the deflecting plates (or deflecting coils) of the tube are indicated by 37, and the trace unblanking cathode is indicated by 38. The circuit components 39, 40, 41 and 44 are the conventional basic elements of an ultrasonic-imaging apparatus, such as a clock 39 which determines the basic repetition rate of the ultrasonic impulses from head 2, a time delay 40, a pulser 41, and an ultrasonic transmitter-receiver circuit 44.

As already described, in the case of the output signal of the resolver 17 or 18, respectively, the angular information is contained in the amplitude of the respective a.c. signal. The angular information should be determined with great accuracy. For this reason, an amplitude modulation of high quality is also desired. A simple peak value detector is only barely suitable given these requirements, since, in the case of the latter, the polarity information of the different angle functions becomes lost and is capable of being electronically regenerated only by means of additional members. In addition, in the case of small sine- and cosine-values, the required precision can be achieved only with considerable technical outlay.

Figure 6:
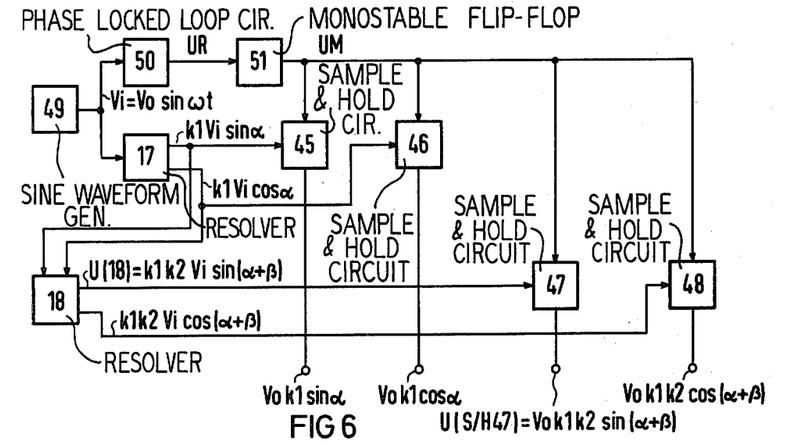
FIG. 6 illustrates a preferred exemplary embodiment of the demodulators e.g. for the basic circuit diagram of FIG. 5.

FIG. 6 illustrates an exemplary embodiment of a demodulator circuit for the purpose of highly precise amplitude modulation. The major component is a sample-and-hold circuit whose individual gates 45–48 are actuated by the sine waveform voltage Vi = Vo·sin $\omega$ t of a sine waveform generator 49 via a PLL (phased locked loop)-circuit 50 with a monostable flip-flop 51 connected to the output of circuit 50. In order to avoid phase displacements of the resolver-output signals as compared with this sine-waveform reference voltage Vi, winding-compensated resolvers should preferably be introduced (see also FIG. 8).

Figure 7:
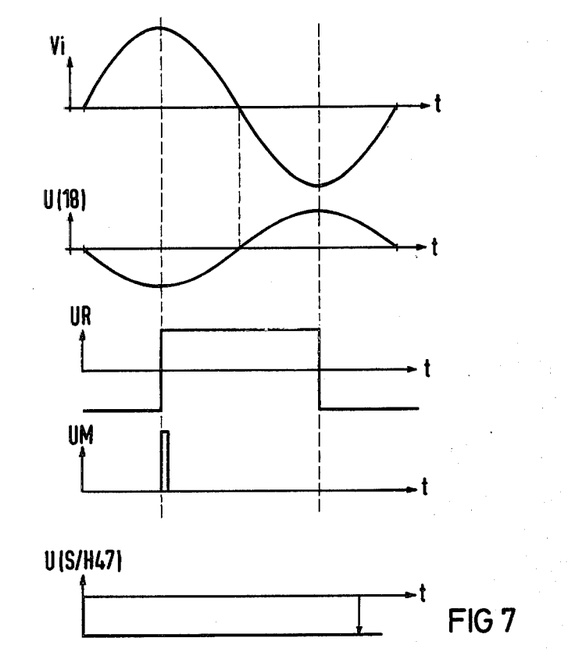
FIG. 7 illustrates a diagram of the voltage waveforms of the signals for controlling the demodulators according to FIG. 6.

Thus, in the exemplary embodiment of FIG. 6, a single reference voltage Vi is delivered to the PLL-circuit 50. The resonant frequency of this circuit 50 is equal to the frequency of the applied reference signal Vi. Thus, a rectangular (or square wave) signal UR occurs at the output of the PLL-circuit 50 which is phase-displaced by 90° relative to the reference signal Vi (FIG. 7). The positive slope of this rectangular signal UR triggers the monostable flip-flop 51 which subsequently supplies a very short rectangular pulse UM. This pulse UM then finally controls (or operates) the gates 45 through 48 of the sample-and-hold circuitry in the sense of demodulation of the applied signals $k_1 V_i \sin \alpha$, $k_1 V_i \cos \alpha$, $k_1 k_2 V_i \sin (\alpha+\beta)$, and $k_1 k_2 V_i \cos (\alpha+\beta)$. Due to this demodulation, the desired sine functions at the outputs of the individual sample-and-hold-gates 45 through 48 result. In the voltage diagram of FIG. 7, for the purpose of a clear overview, only one of these d.c. voltages is shown. The latter relates to the output votage $U(S/H\ 47) = k_1 k_2 V_o \sin (\alpha+\beta)$ at the output of gate 47. The respective input voltage is the output voltage $U\ (18) = k_1 k_2 V_i \sin (\alpha+\beta)$ of the resolver 18.

A PLL-demodulator circuit such as shown in FIG. 6 has the advantage that great fluctuations in the amplitude of the reference signal, as well as frequency changes lying in the capture (or pull-in)- range of the PLL-circuit, hardly or do not at all impair the precision of the system. A 90°-phase displacement between the reference signal and the scan signal leads to the result that the angular information is always obtained in the maximum of this output signal. Since, at this moment, the output signal manifests the least slope (or steepness), the interference-sensitivity at this point will also be minimal. The PLL-circuit, in addition, renders possible a polarity-correct amplitude demodulation, as well as the exact analysis (or evaluation) of great as well as small sine- and cosine-values.

Figure 8:
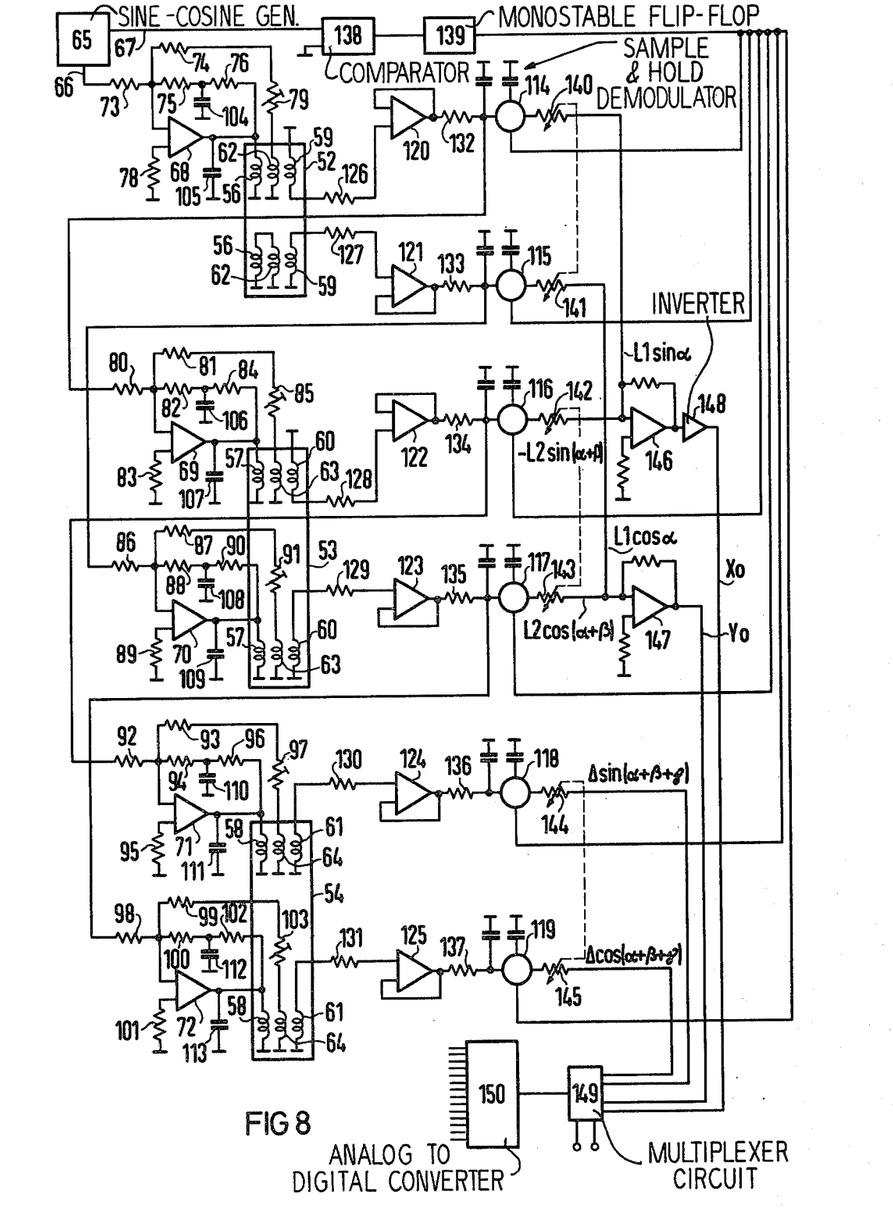
FIG. 8 illustrates an exemplary embodiment of an ultrasonic scanning system comprising a three-arm support according to FIG. 4, which likewise comprises a resolver chain.

FIG. 8 illustrates an exemplary embodiment of an ultrasonic scanning system with a three arm support according to FIG. 4. The basic circuit diagram of FIG. 8 now contains, corresponding to the three joints 14, 15 and 16, of the articulated support of FIG. 4, a resolver chain consisting of a total of three resolvers 52, 53 and 54. The individual resolvers are winding-compensated; i.e., in addition to the stator main windings 56, 57 and 58, and the rotor windings 59, 60, 61, they also additionally comprise compensation windings 62, 63 and 64, respectively, for eliminating phase displacements and temperature influences.

The basic voltage generator is an a.c. voltage generator 65 which, however, in the present instance, in a modification, is designed as a sine-cosine generator. Accordingly, the generator 65 delivers to a first output 66, a sine waveform a.c. voltage, and at an output 67 supplies a cosine waveform voltage of the same amplitude and frequency as the sine waveform voltage. The supply of the sine voltage to resolver 52, and the supply of signals, respectively transmitted, due to the cascade circuit, to the stator windings of the succeeding resolvers 54 and 54, proceed via feedback amplifiers 68, 69, 70, 71 and 72. The feedback amplifiers are, in the manner illustrated, wired with ohmic resistances 73 through 103 as well as capacitances 104 through 113. The intercoupling of the resolvers via the rotor windings, as well as with sample-and-hold-demodulators 114 through 119, proceeds via impedance converters (or buffers) 120 through 125. The impedance converters 120–125 are, in the manner illustrated, wired with ohmic input resistances 126 through 133, as well as HF (high frequency)-interference elimination members 132 through 137. The actuation of the individual sample-and-hold-demodulator circuits 114 through 119 proceeds from the output of the series circuit of a comparator 138 for the rectangular (or square wave) conversion of the cosine waveform of generator 65 (instead of a PLL-circuit) and the monostable flip-flop 139. Via potentiometers 140 through 145, which are respectively mechanically coupled in pairs, the signals indicated in the circuit diagram of FIG. 8 occur. The output signals of the potentiometers 144 and 145 are here directly conveyed to a multiplexer circuit 149; while the output signals of the potentiometers 140 through 145 are supplied to the multiplexer circuit 149 via sum formation units 146 and 147 (an inverter member 148 being connected at the output of the sum-formation unit 146). From this multiplexer circuit 149, the coordinate signals are then, after analog-to-digital-conversion in an A-D-converter 150, retransmitted to the recording cathode ray tube, particularly via an image store.

Figure 9:
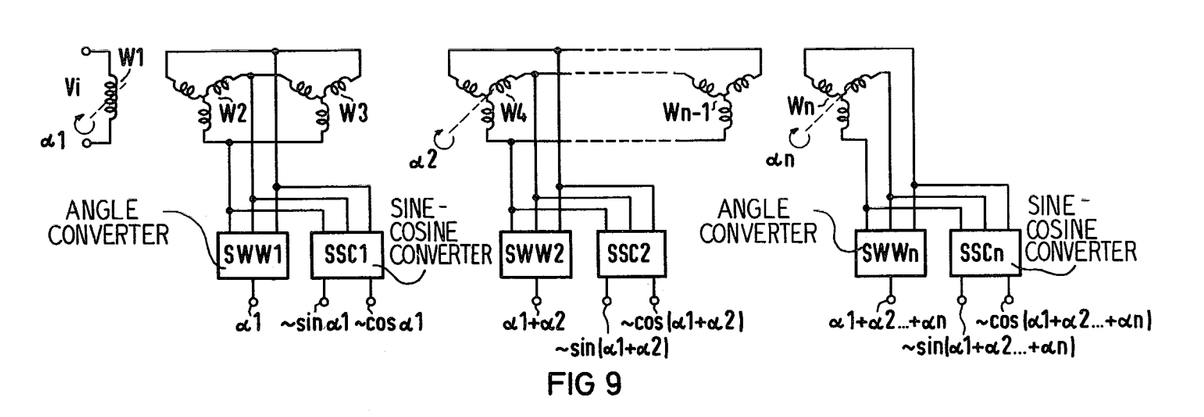
FIGS. 9 and 10 illustrate basic circuit diagrams for synchro control transformer chains.
Figure 10:
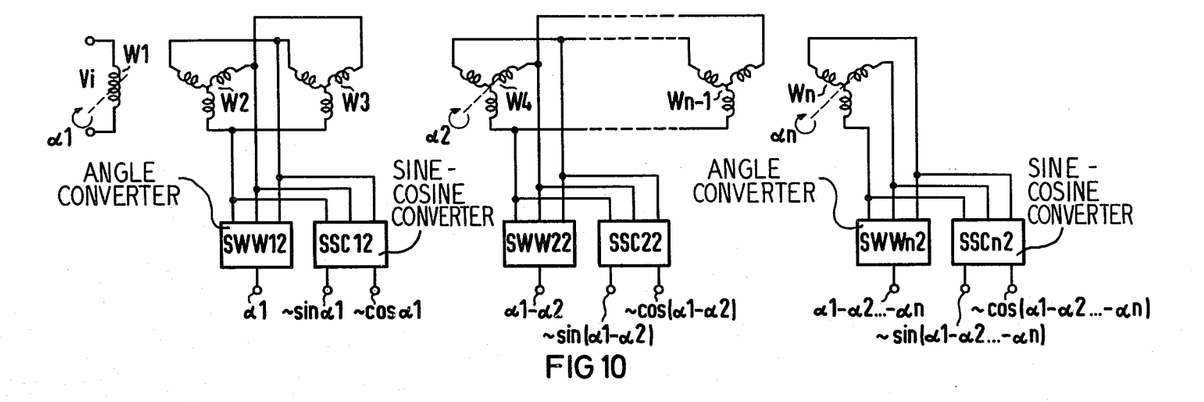

FIGS. 9 and 10 illustrate basic circuit diagrams of synchro control transformers. The windings interconnected in the manner illustrated are referenced by $W_1$ through $W_n$. $V_i$ is again the input a.c. voltage, and $\alpha_1$, $\alpha_2$ through $\alpha_n$ are the angles of rotation. After supply to synchro to angle-converters $SWW_1$ through $SWW_n$, in accordance with the circuit type of FIG. 9, the illustrated angles or angular sums directly result (in analog or digital fashion). In the sample embodiment of FIG. 10, angle or angular differences correspondingly occur at the output of the synchro to angle-converters $SWW_{12}$ through $SWW_{n2}$. Instead of the direct angle-representation, or as a supplement to the latter, sine- or cosine-angular representations, respectively, can also be supplied. The synchro to sine-cosine-converters $SSC_1$ through $SSC_n$ or $SSC_{12}$ through $SSC_{n2}$, respectively, additionally connected into the basic circuit diagrams of FIGS. 9 and 10, serve this purpose.

Figure 11:
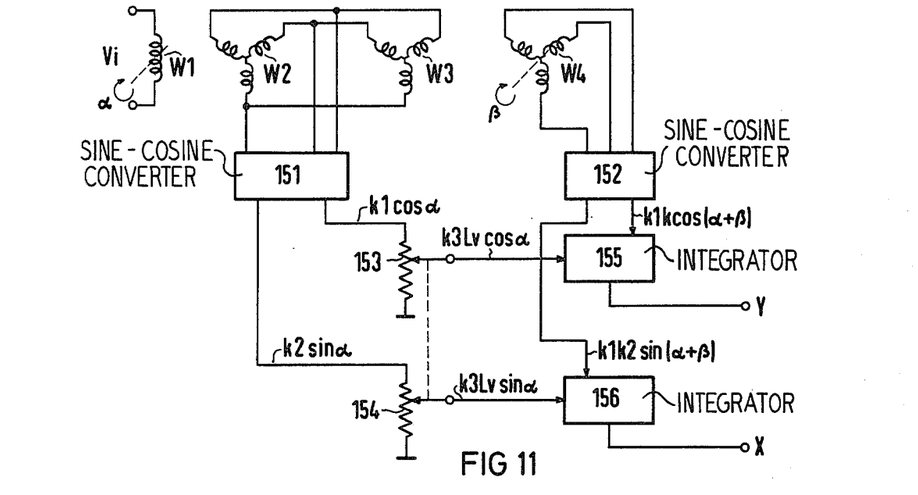
FIG. 11 illustrates the basic circuit diagram of an ultrasonic scanning apparatus for ultrasonic scanning comprising a two arm support according to FIG. 3 which comprises a synchro control transformer chain.

Synchro control transformer chains with synchro to sine-cosine-converters are again particularly well suited for angle-indication in the case of scanning with a two-arm or three-arm support. An exemplary embodiment is illustrated by the basic circuit diagram of FIG. 11 with a synchro control transformer chain for application in the case of a two-arm support according to FIG. 3. This exemplary embodiment is similar to that of FIG. 5 with the resolver chain. In addition to the synchro control transformer chain $W_1$ through $W_4$, the exemplary embodiment of FIG. 11 also comprises two synchro to sine-cosine-converters 151 and 152. The converter 151 supplies the illustrated angular data which are again supplied via potentiometers 153 and 154 as initial conditions to integrators 155 and 156. The supply of the angular sum information proceeds correspondingly by means of connection of the integrators 155 and 156 with the outputs of the converter 152. The data for the X-coordinate and the Y-coordinate, as stated, are present at the output of the integrators.

Figure 12:
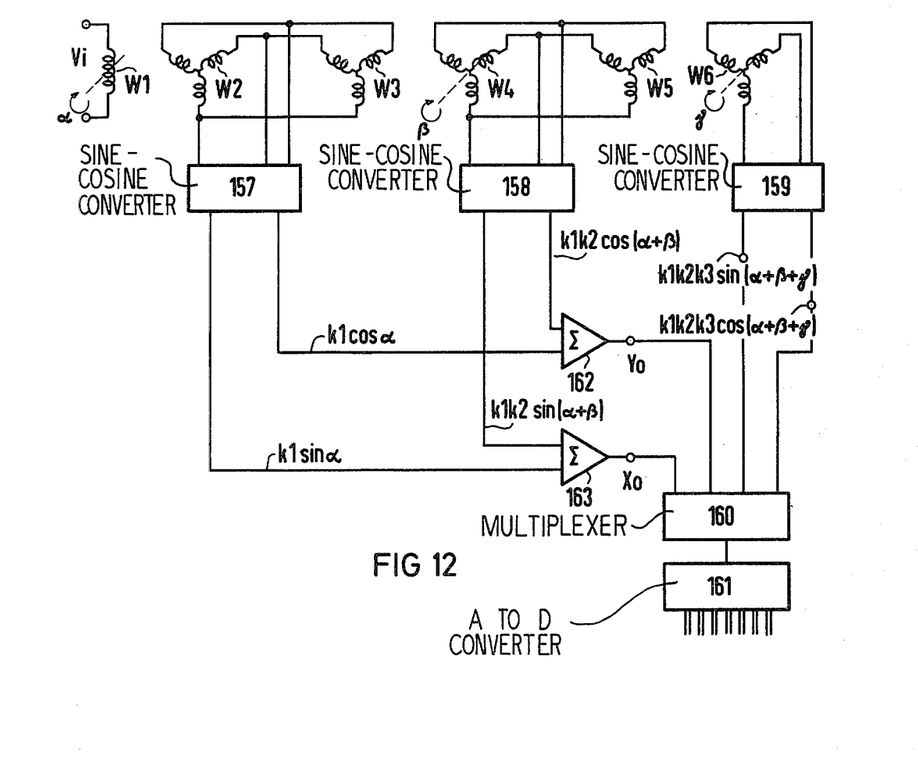
FIG. 12 illustrates the basic circuit diagram of a scanning apparatus for ultrasonic scanning by means of a three arm support according to FIG. 4, which likewise comprises a synchro control transformer chain.

FIG. 12 illustrates an exemplary embodiment of the three-arm support corresponding to FIG. 4. In this basic circuit diagram, three synchro to sine-cosine-converters 157, 158 and 159 are accordingly provided. Corresponding to the exemplary embodiment of FIG. 8 for the resolver chain, the supply to a multiplexer 160 with an analog-to-digital-converter 161 at the output of the multiplexer proceeds by means of direct connection with the converter 159, on the one hand, and connection with the converters 157 and 158 via sum-formation units 162 and 163, on the other hand.

It will be apparent that many modifications and variations may be effected without departing from the scope of the novel concepts and teachings of the present invention.

We claim as our invention:

1. Apparatus for object scanning, in particular, an ultrasonic scanning apparatus, comprising an articulated support having a plurality of pivotal joints and operable for supporting at least one scan head, particularly an ultrasonic head, for a scanning operation, and comprising a scan coordinate determining system with angle indicators for coupling with the pivotal joints of the support and operable for determining coordinates of the scanning operation for any spatial position of the scan head in dependence upon angular signals of the angle indicators, said angle indicators comprising synchro means (17, 18; 52, 53, 54) coupled with the respective pivotal joints (7, 9; 14, 15, 16) of the articulated support (1a; 1b) during a scanning operation and having synchro outputs for providing synchro output signals as a function of trigonometric functions of the angular values ($\alpha, \beta; \alpha, \beta \gamma$) representing the angular condition of the support, said system comprising a purely electronic cascade interconnection of said synchro means for cascade energization thereof, and conversion means connected with the synchro outputs for converting said synchro output signals into combined angular functions of combined angular values representing functions of combinations of the angular values, said conversion means comprising demodulators (27, 28, 32, 33; 114 through 119) connected to the synchro outputs of the synchro means for demodulating the synchro output signals and for supplying demodulated signals in accordance therewith, characterized in that said system comprises input supply means for supplying an input alternating current supply signal (Vi) to a first synchro means of said cascade interconnection of said synchro means, the demodulators comprising sample and hold circuitry (45–48; 114–119) which is keyed for the purpose of demodulation of the synchro output signals of the synchro means of the cascade interconnection in dependence upon the input alternating current supply signal.

2. Apparatus according to claim 1, characterized in that said input supply means comprises a simple vine waveform generator (49), the sample and hold circuitry having a phase locked loop circuit (50) and a following monostable circuit (51) operated by the input alternating current supply signal and controlling the keying of said sample and hold circuitry.

3. Apparatus according to claim 1, characterized in that said input supply means comprises a sine/cosine generator (65), and said sample and hold circuitry having a comparator (138) and a following monostable circuit (139) coupled with said sine/cosine generator for controlling the keying of said sample and hold circuitry.

* * * * *